(12) United States Patent
Geis et al.

(10) Patent No.: US 6,979,321 B2
(45) Date of Patent: Dec. 27, 2005

(54) APPARATUS FOR INSERTING PARTICLES INTO TISSUE, IN PARTICULAR MUSCLE TISSUE

(75) Inventors: John S. Geis, Grunwald (DE); Michael Braun, Backnang (DE)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 50 days.

(21) Appl. No.: 10/181,741

(22) PCT Filed: Jul. 11, 2001

(86) PCT No.: PCT/US01/41342

§ 371 (c)(1),
(2), (4) Date: Jul. 19, 2002

(87) PCT Pub. No.: WO02/04063

PCT Pub. Date: Jan. 17, 2002

(65) Prior Publication Data

US 2003/0014012 A1    Jan. 16, 2003

(30) Foreign Application Priority Data

Jul. 11, 2000 (DE) ............................... 200 12 003

(51) Int. Cl.[7] ........................ A61M 5/00; A61M 29/00; A61M 5/178

(52) U.S. Cl. ................ 604/181; 604/104; 604/164.01; 604/107

(58) Field of Search ............................. 604/57, 102.01, 604/104–107, 264, 523, 181, 187, 137, 272, 604/214, 236, 231

(56) References Cited

U.S. PATENT DOCUMENTS

| 1,719,428 | A |   | 7/1929 | Friedman |
|---|---|---|---|---|
| 3,799,172 | A |   | 3/1974 | Szpur |
| 3,946,741 | A | * | 3/1976 | Adair .......................... 604/105 |
| 4,154,242 | A |   | 5/1979 | Termanini |
| 4,315,513 | A | * | 2/1982 | Nawash et al. ............. 604/537 |

(Continued)

FOREIGN PATENT DOCUMENTS

FR    FR 2 511 600 A    2/1983

(Continued)

OTHER PUBLICATIONS

Search Report for International Patent No PCT/US01/41342; filed Jul. 11, 2001, Geis, et al. Apparatus For Inserting Particles Into Tissue, In Particular Muscle Tissue.

*Primary Examiner*—Nicholas D. Lucchesi
*Assistant Examiner*—Matthew F. DeSanto
(74) *Attorney, Agent, or Firm*—Blakely, Sokoloff, Taylor & Zafman LLP (57) ABSTRACT

An apparatus for inserting particles (P) into a tissue (G), in particular a muscle tissue, wherein the apparatus (10) essentially represents a tubular body (7) with one closed end and comprises at least one sleeve (8), at least one positioning element (1), at least one outlet area (2), which extends over the entire circumference of the tubular body (7), at least one thrust means (4) for the particles (P), as well as an actuating device for the outlet area (2), and wherein the outlet area (2) is formed by a plurality of flexible elements (6), which are at least attached to the sleeve (8), which butts against the outlet area (2) in the axial direction, or the positioning element (1) in such a way, that in a tense condition the diameter of the outlet area (2) is larger than the diameter of the sleeve (8), and openings are present between the elements (6).

8 Claims, 6 Drawing Sheets

U.S. PATENT DOCUMENTS

| | | | | |
|---|---|---|---|---|
| 4,808,163 A | * | 2/1989 | Laub | 604/105 |
| 5,232,440 A | * | 8/1993 | Wilk | 604/543 |
| 5,423,744 A | | 6/1995 | Gencheff et al. | |
| 5,514,112 A | * | 5/1996 | Chu et al. | 604/267 |
| 6,221,006 B1 | | 4/2001 | Dubrul et al. | |

FOREIGN PATENT DOCUMENTS

| | | |
|---|---|---|
| WO | WO 99/48550 A | 9/1999 |

* cited by examiner

APPARATUS FOR INSERTING PARTICLES INTO TISSUE, IN PARTICULAR MUSCLE TISSUE

CROSS-REFERENCE TO RELATED APPLICATION

Applicant hereby claims priority based on German Utility Model Registration No. G 200 12 003.4 filed Jul. 11, 2000, entitled "Apparatus for Inserting Particles into Tissue, in Particular Muscle Tissue" which is incorporated herein by reference.

FIELD OF INVENTION

The present invention relates to an apparatus for inserting particles into a tissue, in particular muscle tissue.

For example, for administering medicine or for inserting cell cultures in the body of a human being or an animal, it can be necessary to introduce those agents, which were only recited as examples and will hereinafter generally be referred to as particles, directly into the tissue. For treatment of the heart it can even be necessary to insert the particles directly into the cardiac muscles.

BACKGROUND OF THE INVENTION

Apparatus are already known, which cut channels into the tissue, in order to provide a space for the reception of the particles. These apparatus are, however, disadvantageous in that, as soon as the apparatus is withdrawn from the drilled channel, the tissue can only contract itself to a limited extent and thus the particles can escape from the channel. If no channel is drilled there is not sufficient space for the particles in the tissue.

Furthermore with tissues, which are in constant motion, such as the tissue of the cardiac muscle, it is difficult to position and affix the apparatus for the insertion of the particles.

The problem underlying the present invention is therefore to provide an apparatus for inserting particles into a tissue, which apparatus can be ideally positioned and affixed and which allows the insertion of particles into the tissue, without the danger of the particles escaping from the tissue or being pressed out of the tissue, once the apparatus has been removed.

SUMMARY OF THE INVENTION

The invention is based on the finding, that this problem can be solved by an apparatus, which is positioned and affixed by a tip and by means of which a cavity can be provided in the interior of the tissue.

The problem is solved according to the invention by an apparatus for inserting particles into a tissue, in particular a muscle tissue, wherein the apparatus essentially represents a tubular body with one closed end and comprises at least one sleeve, at least one positioning element, at least one outlet area, which extends over the entire circumference of the tubular body, at least one thrust means for the particles, as well as an actuating device for the outlet area, and wherein the outlet area is formed by a plurality of flexible elements, which are at least attached to the sleeve, which butts against the outlet area in the axial direction, or the positioning element in such a way, that in a tense condition the diameter of the outlet area is larger than the diameter of the sleeve, and openings are present between the elements.

The positioning element serves for positioning the apparatus and facilitates the penetration into the tissue, where it is thereby affixed. In the tubular body a space is formed between the end of the positioning element, averted to the distal end of the apparatus, and the thrust means, which serves for receiving the particles to be introduced into the tissue. If the apparatus is brought into a tense condition, which will be described later in detail, the outlet area is extended in the radial direction, whereby openings, through which the particles can emerge out of the space described above and can penetrate into the tissue, are formed between the flexible elements forming this area.

The emerging of the particles is supported by the thrust means. These means serve to force the particles through the openings formed in the outlet area. The diameter of the outlet area in the tense condition is larger than the one of the sleeve, which is adjacent thereto. The tissue in this area will therefore be pushed back in the tense condition, i.e., will be expanded. Even after relaxing the apparatus and removing the apparatus from the tissue, the tissue cannot contract itself entirely to the original form, because of the particles, which have been forced out of the outlet area and because of the cavity formed due to the expansion of the outlet area, so that at least a part of the particles remains securely in the tissue and depending on the application can penetrate into the tissue or can remain in the cavity.

Preferably the positioning element is a needle tip. This needle tip can ensure a rapid insertion of the apparatus into the tissue and can thus avoid a sideslip, as it would occur with an apparatus, where the insertion would take place slowly. According to the invention, the needle tip can have a tapered portion, which extends from the outlet area to the distal end of the apparatus. In such an embodiment, the length of the tip must be chosen accordingly, in order to achieve a small increase in diameter from the distal end to the outlet area over small axial distances. If the increase of the diameter over small axial distances would be too large, the insertion into the tissue would be more difficult.

However, it is also in line with the invention, if the needle tip is formed with a tapered, conical portion, an adjacent cylindrical portion of smaller diameter and finally a needle point running to a point at the distal end. In this embodiment the needle point running to a point and the cylindrical portion allow facilitated insertion into the tissue and the tapered portion provides for a continuous transition from the smaller diameter of the cylindrical portion to the comparatively larger diameter of the outlet area and sleeve, respectively.

The needle tip is preferably arranged in such a way, that its axis coincidences with the axis of the apparatus. However, it is also possible to provide the positioning element in the proximity of the end, e.g., at the side of the tip, in particular, if the positioning element has a shape different from the described needle tip.

The elements of the outlet area can have different shapes. In one embodiment the elements are formed as stripes of a flexible material and are arranged in a spiral or helical arrangement. With such a helical arrangement of the elements, their flexibility can be sustained. An ideally formed basket can form with such a helical arrangement in the tense condition, if the elements are attached on both sides, i.e., towards the sleeve and the positioning element. At the position of the largest diameter, this basket exhibits the biggest distances between the stripe-shaped elements and in addition exhibits a high stability. Especially, if the apparatus should be used for inserting particles into a cardiac muscle or any other strong muscle tissue, it is important that this area exhibits a stability, which can withstand the external pressure applied on the outlet area and can ensure an expansion of the tissue.

The elements of the outlet area, in particular long struts, can also be arranged in such a way, that their longitudinal axis is parallel to the axis of the apparatus. In this embodiment, however, the force for actuating the outlet area is higher, than with a helical arrangement of the elements and the actuating devices must thus to be chosen to be capable of applying the required force to the elements of the outlet area.

In the relaxed condition, the outlet area forms a closed area, i.e., the elements abut close to each other or overlap. In order to ensure the sealing of this area and to thereby prevent escaping of smaller particles during the insertion of the apparatus into the tissue, the apparatus can also have two layers of elements. These two layers are preferably formed as tubes and are radially spaced from each other. In this embodiment, the direction of the spiral winding of the elements of the inner layer can be opposite to the direction of the spiral winding of the elements of the outer layer. It is also possible to provide different angles of inclination of the spiral windings in the two layers. By providing two layers, two tubular walls for the outlet area are formed, which prevent an undesired early escape of particles.

The stripes or struts used as elements, preferably, have an essentially rectangular shape. It is, however, also possible to use stripes which narrow over their length towards their middle.

In a further embodiment the elements of the outlet area form a net. The individual elements in this embodiment are interconnected with each other such, that, also in the expanded condition, i.e., in the condition where the apparatus is tense, joints are present by means of which the cohesion of the elements is ensured. Between these joints net- or grid-struts are provided, which connect them and in the relaxed condition form a closed surface together with the joints. The net- or grid-struts can have different shapes. Since in the tense condition, however, a pressure has to be applied by the net to the tissue surrounding the outlet area, they have to be stable and may not cause damaging of the tissue. Due to these requirements preferably flat wires are used. The connection between the struts is preferably formed by meshes, since these allow an expansion and contraction of the outlet area.

The above mentioned tense condition of the apparatus is achieved by operating the actuating device for the outlet area. This actuating device is preferably a sliding device. It is connected to the sleeve, which is positioned at the side of the outlet area, which is averted to the positioning element, and can move the sleeve axially. In this embodiment, for example, an extension of the sleeve can form the sliding device. By moving the sliding device in the direction of the positioning element, the distance between the two intermediate areas, in which the outlet area is located, is decreased and a force is thus applied on the outlet area. This leads to the bending of the elements and to them separating from each other in their axial middle, whereby the clearances between the elements form the openings for the outlet of the particles.

In order to not change the position of the entire apparatus within the tissue by actuating of the sliding device, i.e., to not move the apparatus accidentally further into the tissue, the actuating device preferably comprises a sliding device with means, which runs within the tubular body along the axis thereof and which is connected to the positioning element. By these means a tensile force can be applied, which, together with the above mentioned compression force applied via the sleeve, can lead to a targeted activating of the outlet area, i.e., expansion of the area and enlarging of the openings and spaces, respectively, without changing the position of the apparatus within the tissue.

These means can be a taut wire or can be represented by an inner tube arranged inside the tubular body of the apparatus.

As described above, the particles are, as soon as the apparatus has been introduced into the tissue and stress has been applied, pressed out of the tubular body via the openings in the outlet area, by means of thrust means for the particles. These thrust means preferably comprise a piston. The diameter of the piston and of the head of the piston, respectively, is determined by the inner diameter of the sleeve.

The inventive apparatus can be used for versatile applications. With the apparatus both, tissues from the outside, e.g., the skin, as well as tissues inside of the body, such as the inner organs, in particular the heart, can be treated. In the latter case the apparatus preferably represents a catheter, which is guided in a guide catheter. In this embodiment the actuating device for the outlet area and the activating device for the thrust means are arranged at the end of the catheter, which is opposite to the distal end, at which the positioning element is located (the proximal end).

Thereby the doctor is enabled to specifically control, from the outside, the expansion of the outlet area and the outlet of the particles.

Basically those catheters, which are already known, can be used as catheters. The design of catheters, as well as their handling, is known in the field of medical engineering and will therefore not be further explained at this point. The catheter for the inventive apparatus, however, exhibits at its distal end the components of the apparatus, in particular the positioning element and the outlet area. The guide catheter encloses the catheter, which carries the apparatus or represents the apparatus, respectively, and serves for an easier insertion of the inner catheter into the vessels and prevents the occurrence of injuries or irritations, which can occur due to the back-and forth-movement of the inner catheter, e.g., for tensioning and relaxing the apparatus.

Before the apparatus is inserted into the tissue and first into the vessel leading to the location to be treated, respectively, the apparatus will be loaded with the corresponding particles, e.g., pharmaceuticals, cell cultures in the form of pellets, etc. For this purpose the apparatus preferably has a charging port, which is provided in the wall of the sleeve spaced from the outlet area. Via this charging port the particles can be brought close to the outlet area, which is of special interest for apparatus, which represent catheters and can accordingly be of considerable length. If for example cell cultures shall be brought into the cardiac muscle, the catheter will have a length of about one meter and at the same time the cell cultures are sensitive substances, which can be damaged by a long residual time in the catheter and by too frequent contacting with and rubbing along the walls of the catheter. In particular in such applications the providing of a charging port close to the outlet area will be of advantage.

The invention will hereinafter be described in more detail, by making reference to the enclosed drawings, which represent examples of embodiments of the invention, wherein:

DETAILED DESCRIPTION

Figure 1:
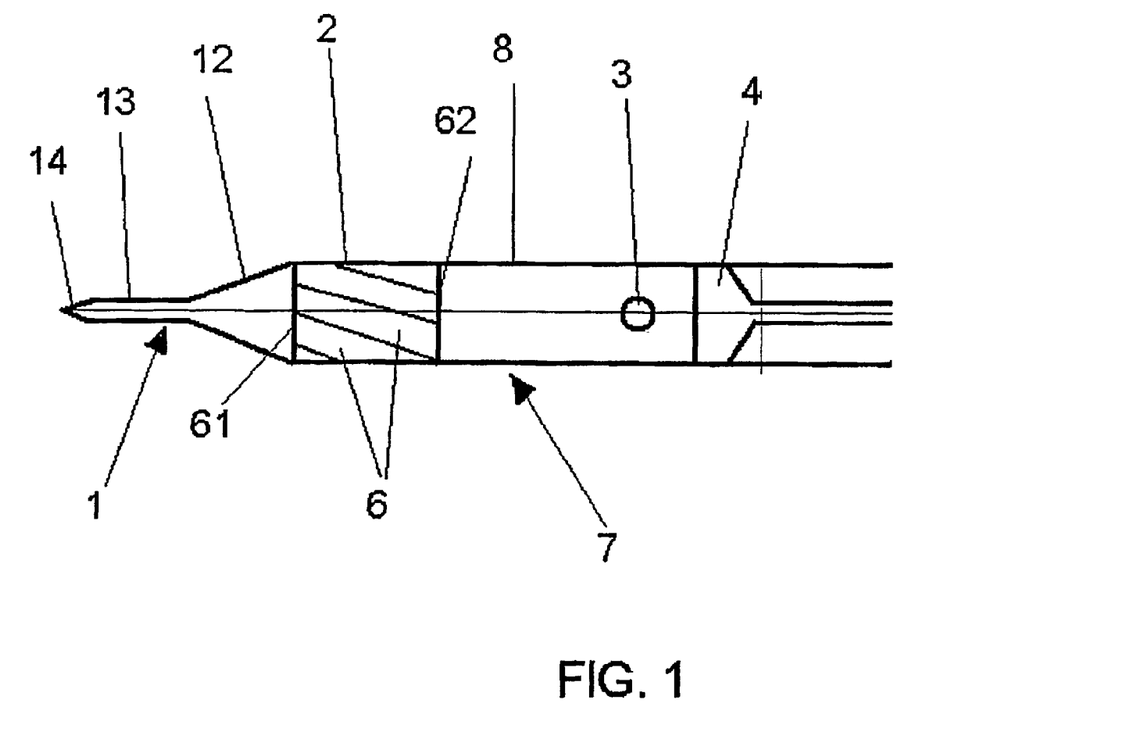
FIG. 1 shows a schematic view of an embodiment of the apparatus according to the invention in the relaxed, unloaded condition.

In FIG. 1 an embodiment of the apparatus 10, according to the invention, is shown schematically. The apparatus 10 has at its distal end a positioning element 1. This element 1 is represented by a needle tip. In the embodiment, as shown, the needle tip comprises a portion 12, which is tapered in the direction of the distal end, an adjacent cylindrical portion 13 of small diameter and finally a needlepoint 14, which runs to a point at the distal end. Adjacent to this positioning element 1 is an outlet area 2. This area 2 shows a plurality of elements 6, which in the embodiment as shown are arranged diagonal to the axis of the tubular body 7 and which form a closed superficies. The elements 6 are connected at their one end 61 with the positioning element 1 and at their other end 62 with the sleeve 8. The sleeve 8 extends in axial direction to any length. At the axial end of the sleeve 8, which is opposite to the end adjacent to the outlet area, an actuating device (not shown) is provided. By means of this actuating device, on the one hand, the sleeve 8 can be slid axially in the direction of the outlet area 2. On the other hand a taut wire 5, which extends along the axis of the sleeve 8, can be stressed with a tensile force by this device. The taut wire 5 extends from the end, at which the actuating device is located to the distal end of the apparatus, i.e., to the positioning element 1. In the embodiment as shown, the taut wire 5 is affixed to the inside of the needle tip of the positioning element 1. It is, however, also within the meaning of the invention to design the positioning element 1 not as a hollow body, but as a solid body.

In the sleeve 8 a port 3 is provided, which is located in a certain distance from the outlet area 2. The distance between the charging port 3 and the outlet area 2 is essentially determined by the amount of particles to be introduced into the tissue. This distance can for example be in the range of 1 cm to 7 cm. Furthermore, a piston 4 is guided in the sleeve, which, on the end facing the outlet area, shows a disc, the diameter of which corresponds approximately to the interior diameter of the sleeve 8. The disc can be provided with sealing means (not shown) at its circumference, e.g. in the form of a silicone ring. In addition, at an opening, which should be provided in the middle of the disc of the piston 4, to allow the passage of the taut wire 5 there through, a sealing, e.g., in the form of a silicone sleeve, can also be provided. Thereby a space is created between the piston 4 and the positioning element 1, which is enclosed by a part of the sleeve 8 and the outlet area. In the position of the piston 4 as shown, the port 3 is within the area of this space. Via this port 3 the space can therefore be filled with particles.

After the space essentially has been filled with particles, the piston 4 will be moved in the direction of the outlet area 2, until the disc of the piston has reached a position shortly behind the port 3, i.e., between the port 3 and the outlet area 2, close to the port 3.

The port can be covered by sealing means, such as a silicone membrane, through which the particles can be fed to the sleeve with, for example, a syringe. Depending on the nature of the particles, in particular on their state of aggregation, the port can, however, also be represented by a simple hole, through which for example gel-like particles can be fed to the apparatus, when the apparatus is in a horizontal position.

Figure 2:
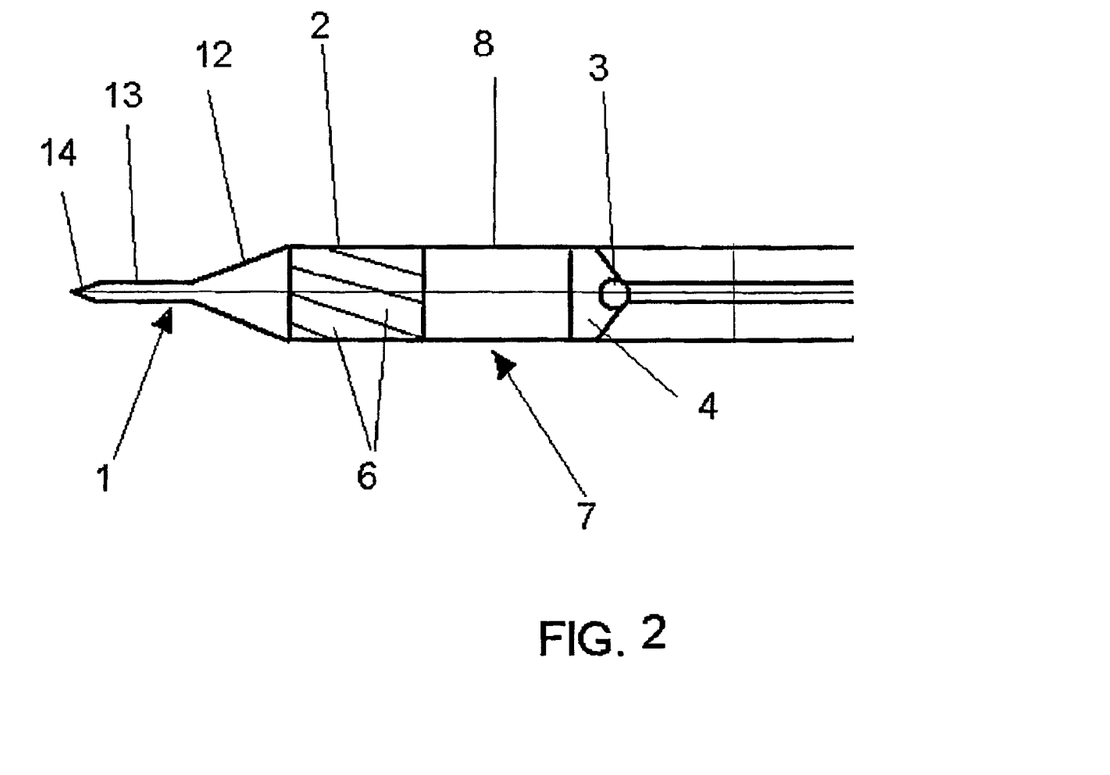
FIG. 2 shows a schematic view of the embodiment of FIG. 1 in the relaxed, loaded condition and before insertion into the tissue.
Figure 3:
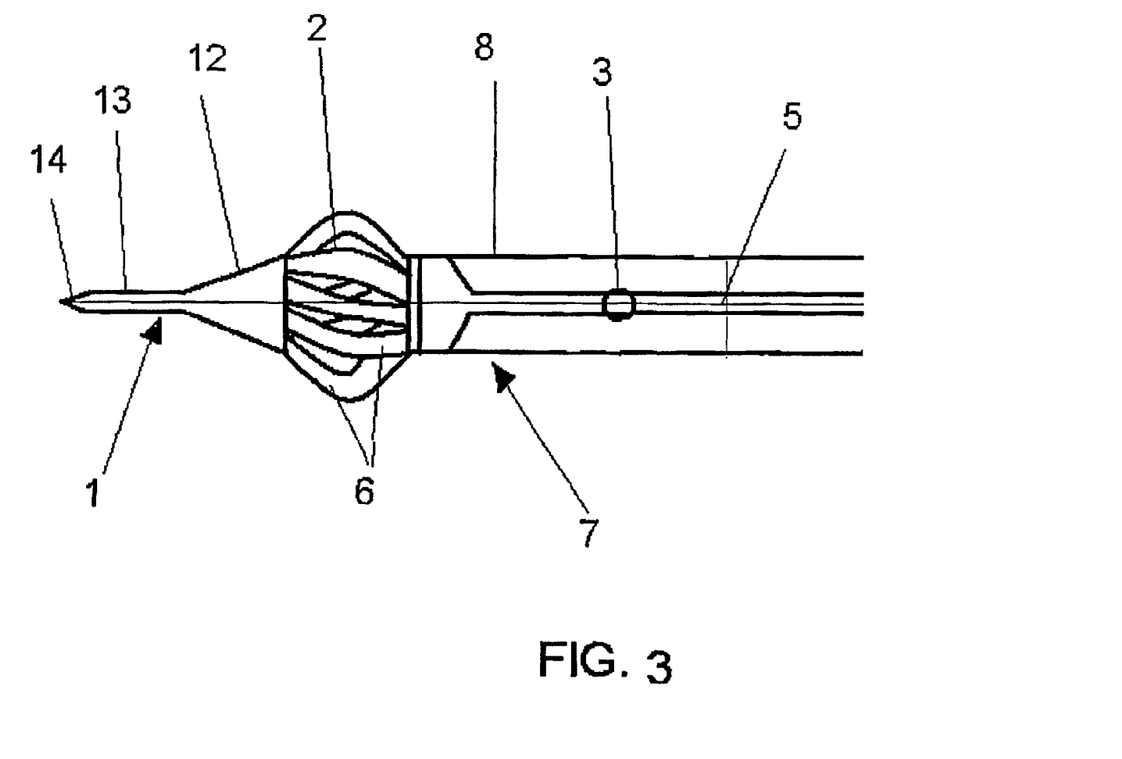
FIG. 3 shows a schematic view of the embodiment of FIG. 1 in the tense condition, during the outlet of the particles.

In FIG. 2 the condition at which the disc of the piston 4 is shortly behind the port 3, is shown schematically. If at that point the actuating device is activated, by means of pulling of the taut wire 5 and, where applicable, by applying pressure on the sleeve 8, the distance between the sleeve 8 and the positioning element 1 will be decreased. Thereby (FIG. 3) the elements 6 of the outlet area 2 will bend outwards. Gaps are formed between the elements wherein the width increases from the sleeve 8 to the middle of the outlet area to then decrease again towards the positioning element 1. By means of these gaps openings are provided, through which the particles can emerge. In order to remove the particles as completely as possible from the apparatus and in order to transfer them to the tissue, the piston 4 will be pushed further in the direction of the outlet area 2. The position shown in FIG. 3 preferably represents the final position of the piston 4. If the piston 4 is moved further, the outlet area 2 will come into contact with the hollow space located behind the disc of the piston 4 and the particles, which were to be pushed into the tissue, would escape via this hollow space into the sleeve 8.

Figure 4:
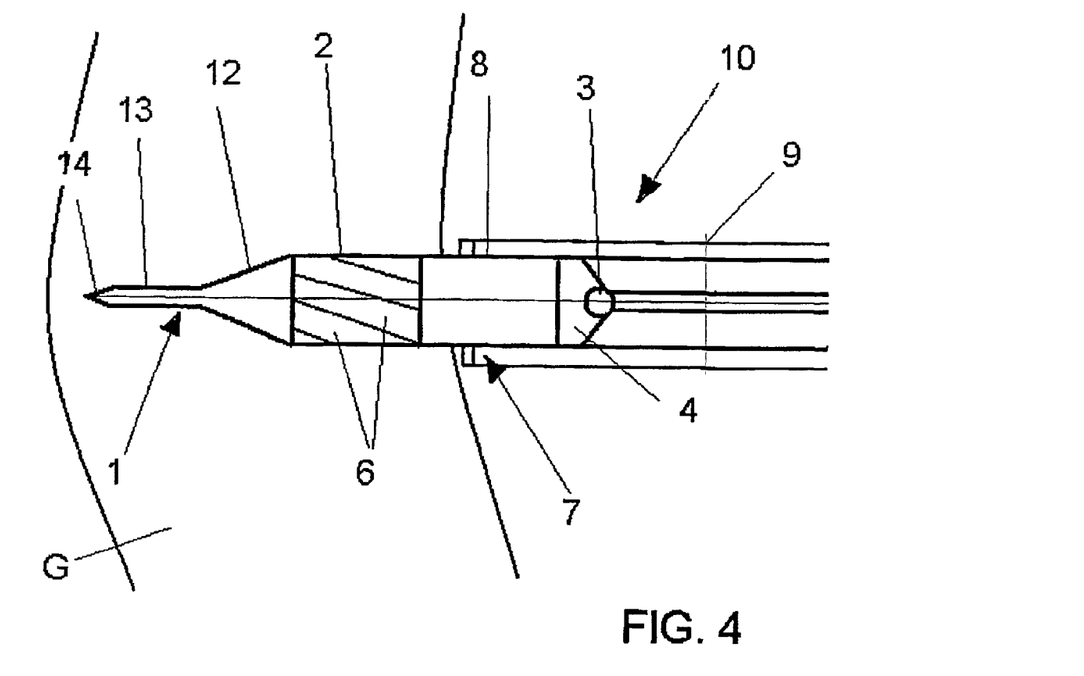
FIG. 4 shows a schematic view of a further embodiment of the apparatus according to the invention with a guide catheter in the relaxed loaded condition, inserted into the tissue.
Figure 5:
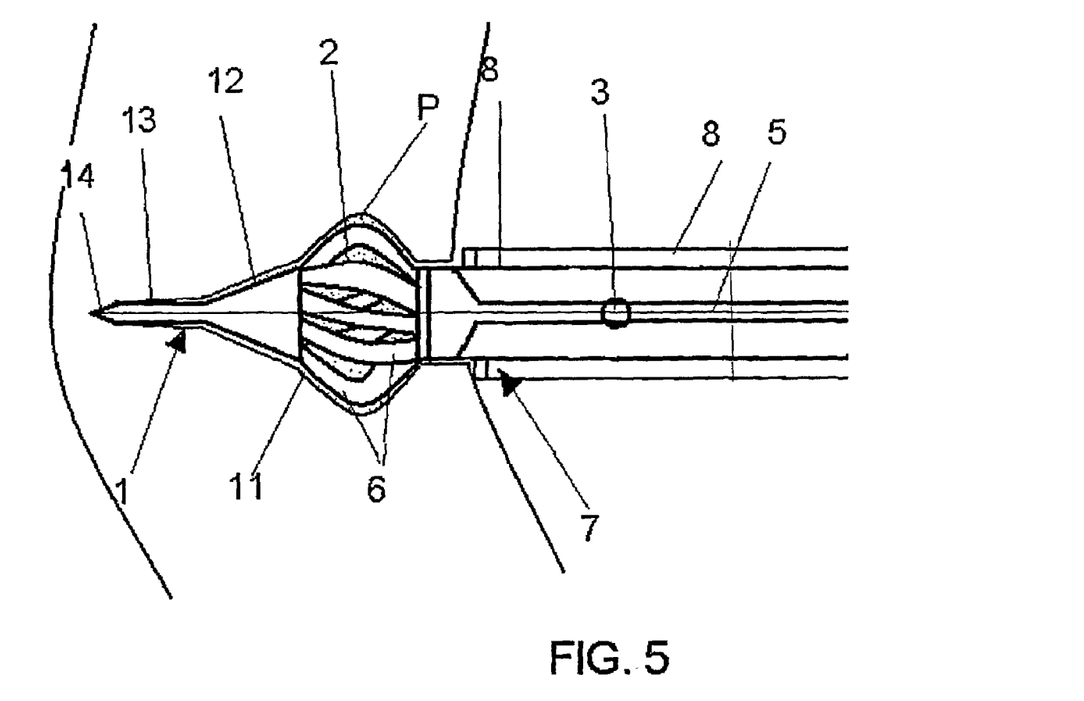
FIG. 5 shows a schematic view of the embodiment of FIG. 4 in the tense condition, inserted into the tissue, during the outlet of the particles.
Figure 6:
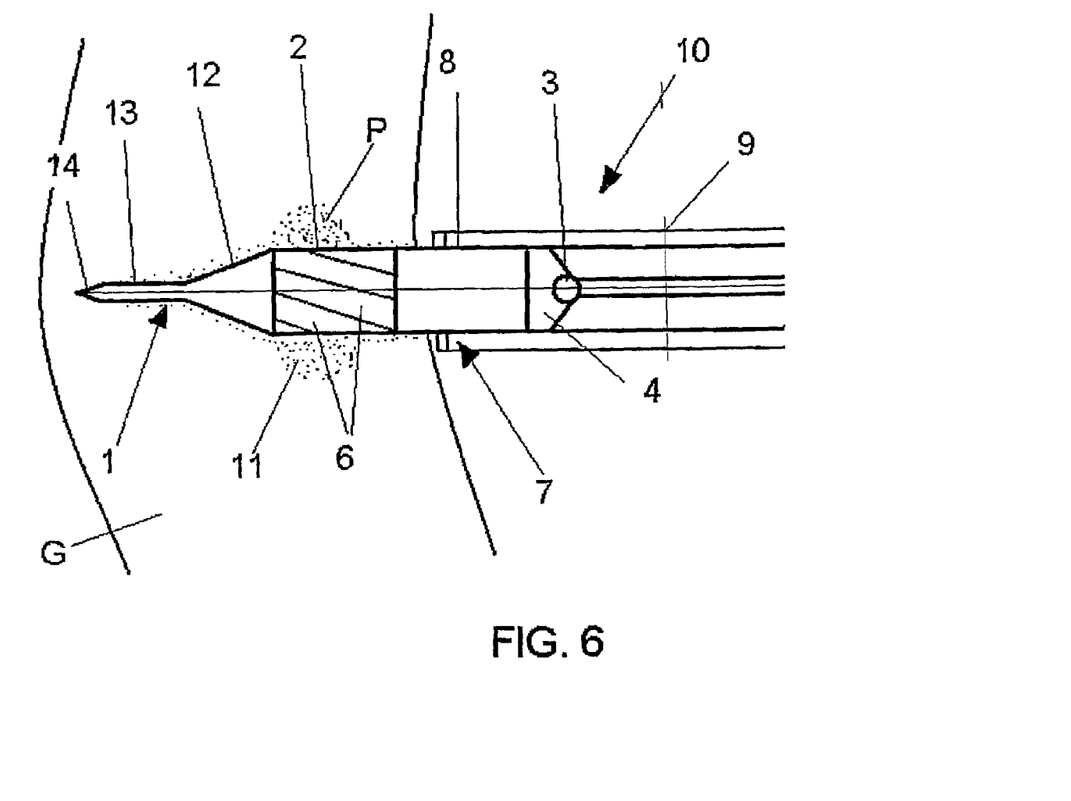
FIG. 6 shows a schematic view of the embodiment of FIG. 4 in the relaxed, discharged condition, prior to removal of the apparatus from the tissue.

In FIGS. 4 to 6 the same conditions as in FIG. 1 to 3 are shown. In this embodiment, however, the apparatus has the form of a catheter, which is guided in a guide catheter 9, and the tissue G, into which the apparatus 10 is introduced, is indicated schematically. In particular from FIGS. 5 and 6 (during the insertion of the particles and after relaxation of the apparatus, respectively) it can clearly be derived, how the particles P enter into the cavity 11 generated by the radial extension of the outlet area 2.

In one embodiment, corresponding to the shown embodiments, the outlet area can be connected directly to the tapered positioning element or, in a further embodiment, it can be connected to a cylindrical section of the positioning element, which is adjacent to the tapered portion of the positioning element. As the dimensions are limited by the thickness of the tissue to be treated, the position shown in the illustrated embodiments will in general be referred.

Depending on the field of application, the apparatus can be made of different materials. Metals and plastic, which are known from medical engineering, can be used. It is preferable to form the sleeve, in particular in the area between the charging port and the proximal end of the apparatus of a highly elastic material, while the area of the apparatus, where the positioning element, the outlet area and the part of the sleeve between the outlet area and the charging port, are arranged should be made of a material of a higher stiffness. This stiffness is necessary for the elements of the outlet area, in order to be able to act against the force, which is applied thereto by the tissue. The positioning element has to be of a sufficient stiffness, in order to allow for a well-aimed introduction in the tissue and a secured fastening. Finally the part of the sleeve, which is between the charging port and the outlet area should be relatively stiff, in order to allow a guiding of the piston along the inside of the sleeve in this area without blocking, which would not be possible at an extreme bending of the section. The said part of the sleeve should therefore be made of an inherent stable material, such as metal. Due to the stiffness of this section also the length thereof is limited. For the introduction into the tissue the apparatus has to be able to follow the course of the vessels, such as blood vessels, and the inner shape of the organs, such as the heart, without damaging either of them. The length of the part which comprises the outlet area, and the section of the sleeve between the charging port and the outlet area, depending on the application, can for example be 2 to 10 cm, preferably 2 to 6 cm.

What is claimed is:

1. An apparatus for inserting particles into a tissue, in particular muscle tissue, the apparatus comprising: a tubular body with one closed end and comprises at least one sleeve, at least one positioning element, wherein the positioning element represents a needle tip, at least one outlet area for the particles, which extends over the entire circumference of the tubular body, at least one piston for pressing the particles, as well as at least one actuating device for the outlet area, the actuating device coupled to the positioning element by a wire, the wire passing through an opening within the piston, and wherein the outlet area is formed by a plurality of flexible elements, which are at least attached to the sleeve, which butts against the outlet area in the axial direction, or the positioning element in such a way, that in an actuated state, a tensile force is applied by the actuating device to the wire and the diameter of the outlet area is larger than the diameter of the sleeve, and openings are present between the flexible elements.

2. The apparatus of claim 1, wherein the flexible elements of the outlet area are stripes of a flexible material, which are arranged helically.

3. The apparatus of claim 1, wherein the flexible elements of the outlet area form a net.

4. The apparatus of claim 1, wherein the actuating device for the outlet area further represents a sliding device, which is connected to the sleeve, which is located at the side of the outlet area, which is averted to the positioning element, and by means of which pressure can be applied on the outlet area by axial sliding of the sleeve.

5. The apparatus of claim 1, wherein the actuating device runs along the axis of the sleeve.

6. The apparatus of claim 1, wherein the apparatus represents a catheter, which is guided in a guide catheter.

7. The apparatus of claim 1, wherein the apparatus shows a charging port for the introduction of the particles into the apparatus, which port is provided in the wall of the sleeve in a distance from the outlet area.

8. An apparatus for inserting particles into biological tissue, the apparatus comprising:
a tubular body having a sleeve and an outlet area for the particles;
a needle tip coupled to the tubular body, the needle tip to position the apparatus in the biological tissue;
an actuating device coupled to the tubular body, wherein the actuating device is coupled to the needle tip by a wire; and
a piston coupled to the tubular body, the piston to press the particles, the wire passing through an opening within the piston, and wherein the outlet area is formed by a plurality of flexible elements, and wherein the actuating element is capable of applying a tensile force to the wire to cause the condition of the flexible elements to change to a state in which a diameter of the outlet area is larger than a diameter of the sleeve, and wherein openings for release of the particles are between the flexible elements.

* * * * *